US012753362B2

(12) United States Patent
Greenfield et al.

(10) Patent No.: US 12,753,362 B2

(45) Date of Patent: Oct. 6, 2026

(54) MAGNESIUM SULFONATE DETERGENT HAVING IMPROVED COMPATIBILITY WITH FRICTION MODIFIERS

(71) Applicant: Afton Chemical Corporation, Richmond, VA (US)

(72) Inventors: Scott Greenfield, Richmond, VA (US); Jason Bell, Powhatan, VA (US)

(73) Assignee: Afton Chemical Corporation

(*) Notice: Subject to any disclaimer, the term of this patent is extended or adjusted under 35 U.S.C. 154(b) by 0 days.

(21) Appl. No.: 18/411,573

(22) Filed: Jan. 12, 2024

(65) Prior Publication Data

US 2025/0230375 A1 Jul. 17, 2025

(51) Int. Cl.

| | |
|---|---|
| ***C10M 135/10*** | (2006.01) |
| ***C07C 309/31*** | (2006.01) |
| ***C10M 129/76*** | (2006.01) |
| ***C10M 141/08*** | (2006.01) |
| ***C10M 169/04*** | (2006.01) |
| ***C10N 30/00*** | (2006.01) |
| ***C10N 30/04*** | (2006.01) |
| ***C10N 40/25*** | (2006.01) |

(52) U.S. Cl.

CPC ......... *C10M 135/10* (2013.01); *C07C 309/31* (2013.01); *C10M 129/76* (2013.01); *C10M 141/08* (2013.01); *C10M 169/04* (2013.01); *C10M 2203/003* (2013.01); *C10M 2207/289* (2013.01); *C10M 2219/046* (2013.01); *C10N 2030/04* (2013.01); *C10N 2030/52* (2020.05); *C10N 2040/25* (2013.01)

(58) Field of Classification Search

CPC C10M 135/10; C10M 129/76; C10M 141/08; C10M 169/04; C10M 2030/52; C10M 2203/003; C10M 2207/289; C10M 2219/046; C07C 309/31; C10N 2030/52; C10N 2030/04; C10N 2040/25

See application file for complete search history.

(56) References Cited

U.S. PATENT DOCUMENTS

| | | | |
|---|---|---|---|
| 2,237,625 | A | 4/1941 | Olin |
| 2,237,627 | A | 4/1941 | Olin |
| 2,527,948 | A | 10/1950 | Lyon, Jr. et al. |
| 2,695,316 | A | 11/1954 | Mcbride |
| 2,995,569 | A | 8/1961 | Hamilton et al. |
| 3,022,351 | A | 2/1962 | Mihm et al. |
| 3,219,666 | A | 11/1965 | Norman et al. |
| 3,308,166 | A | 3/1967 | Biensan et al. |
| 3,392,201 | A | 7/1968 | Warner |
| 3,471,404 | A | 10/1969 | Myers |
| 3,502,677 | A | 3/1970 | Sner |
| 3,565,804 | A | 2/1971 | Honnen et al. |
| 3,634,515 | A | 1/1972 | Piasek et al. |
| 3,673,090 | A | 6/1972 | Waldbillig et al. |
| 3,697,429 | A | 10/1972 | Engel et al. |
| 3,697,574 | A | 10/1972 | Piasek et al. |
| 3,703,504 | A | 11/1972 | Horodysky |
| 3,703,505 | A | 11/1972 | Horodysky et al. |
| 3,714,042 | A | 1/1973 | Greenough |
| 3,736,357 | A | 5/1973 | Piasek et al. |
| 3,763,244 | A | 10/1973 | Shubkin |
| 3,796,661 | A | 3/1974 | Suratwala |
| 3,816,346 | A | 6/1974 | Coppock et al. |
| 3,873,454 | A | 3/1975 | Horodysky et al. |
| 3,991,056 | A | 11/1976 | Okamoto et al. |
| 4,036,771 | A | 7/1977 | Denis et al. |
| 4,118,329 | A | 10/1978 | Hotten |
| 4,119,549 | A | 10/1978 | Davis |
| 4,119,550 | A | 10/1978 | Davis et al. |
| 4,147,640 | A | 4/1979 | Jayne et al. |
| 4,191,659 | A | 3/1980 | Davis |
| 4,204,969 | A | 5/1980 | Papay et al. |
| 4,209,471 | A | 6/1980 | Dube et al. |
| 4,218,332 | A | 8/1980 | Schwab |
| 4,234,435 | A | 11/1980 | Meinhardt et al. |
| 4,240,958 | A | 12/1980 | Braid |
| 4,282,392 | A | 8/1981 | Cupples et al. |
| 4,285,822 | A | 8/1981 | deVries et al. |
| 4,344,854 | A | 8/1982 | Davis et al. |
| 4,472,306 | A | 9/1984 | Powers et al. |
| 4,537,696 | A | 8/1985 | Beimesch |
| 4,564,709 | A | 1/1986 | Koyama et al. |
| 4,587,368 | A | 5/1986 | Pratt |
| 4,636,322 | A | 1/1987 | Nalesnik |
| 4,711,736 | A | 12/1987 | Horodysky et al. |

(Continued)

FOREIGN PATENT DOCUMENTS

| | | | |
|---|---|---|---|
| EP | 0088453 | A1 | 9/1983 |
| EP | 0041851 | A1 | 3/1984 |

(Continued)

OTHER PUBLICATIONS

Takeuchi et al., Investigation of Engine Oil Effect on Abnormal Combustion in Turbocharged Direct Injection-Spark Ignition Engines, SAE Int., Nov. 2012, vol. 5, Issue 3. (Abstract).

(Continued)

*Primary Examiner* — Latosha Hines

(74) *Attorney, Agent, or Firm* — Honigman LLP

(57) ABSTRACT

The present disclosure provides a method of improving the storage stability of a lubricating composition including overbased magnesium sulfonate detergents by post-treating the detergents with select hydrocarbyl-substituted succinic acid or anhydride compounds.

7 Claims, No Drawings

(56) References Cited

U.S. PATENT DOCUMENTS

| | | | |
|---|---|---|---|
| 4,747,971 | A | 5/1988 | Erdman |
| 4,795,576 | A | 1/1989 | Born et al. |
| 4,857,214 | A | 8/1989 | Papay et al. |
| 4,925,983 | A | 5/1990 | Steckel |
| 4,941,984 | A | 7/1990 | Chamberlin, III et al. |
| 4,954,274 | A | 9/1990 | Zaweski et al. |
| 4,956,122 | A | 9/1990 | Watts et al. |
| 4,966,720 | A | 10/1990 | DeGonia et al. |
| 4,992,183 | A | 2/1991 | Beimesch et al. |
| 5,089,156 | A | 2/1992 | Chrisope et al. |
| 5,114,602 | A | 5/1992 | Petrille et al. |
| 5,266,223 | A | 11/1993 | Song et al. |
| 5,614,480 | A | 3/1997 | Salomon et al. |
| 5,627,259 | A | 5/1997 | Thaler et al. |
| 5,633,326 | A | 5/1997 | Patil et al. |
| 5,643,859 | A | 7/1997 | Gutierrez et al. |
| 5,792,729 | A | 8/1998 | Harrison et al. |
| 5,851,965 | A | 12/1998 | Harrison et al. |
| 5,853,434 | A | 12/1998 | Harrison et al. |
| 5,936,041 | A | 8/1999 | Diana et al. |
| 6,124,247 | A | 9/2000 | Cazin et al. |
| 6,303,546 | B1 | 10/2001 | Hata et al. |
| 8,260,530 | B2 | 9/2012 | Rollinger et al. |
| 8,327,687 | B2 | 12/2012 | Amann et al. |
| 8,543,315 | B2 | 9/2013 | Glugla et al. |
| 9,481,696 | B1 | 11/2016 | Edwards et al. |
| 10,829,713 | B2 | 11/2020 | Abraham et al. |
| 11,034,912 | B2 | 6/2021 | Ritchie et al. |
| 11,214,750 | B2 | 1/2022 | Milner |
| 2002/0165102 | A1 | 11/2002 | Hata et al. |
| 2003/0153469 | A1 | 8/2003 | Ozbalik |
| 2004/0242434 | A1 | 12/2004 | Yagishita et al. |
| 2005/0101496 | A1 | 5/2005 | Loper et al. |
| 2006/0058200 | A1 | 3/2006 | Shaw et al. |
| 2006/0217271 | A1 | 9/2006 | Brown et al. |
| 2007/0184992 | A1 | 8/2007 | Takeuchi et al. |
| 2008/0128184 | A1 | 6/2008 | Loper et al. |
| 2009/0156446 | A1 | 6/2009 | McAtee et al. |
| 2011/0111997 | A1 | 5/2011 | Cook et al. |
| 2011/0213538 | A1 | 9/2011 | Amann et al. |
| 2011/0265761 | A1 | 11/2011 | Amann et al. |
| 2012/0029789 | A1 | 2/2012 | Mehta et al. |
| 2012/0101017 | A1 | 4/2012 | Duggal |
| 2012/0132166 | A1 | 5/2012 | Andoh et al. |
| 2012/0186225 | A1 | 7/2012 | Amann et al. |
| 2013/0035841 | A1 | 2/2013 | Glugla et al. |
| 2015/0322367 | A1 | 11/2015 | Patel et al. |
| 2015/0322369 | A1 | 11/2015 | Patel et al. |
| 2016/0230116 | A1 | 8/2016 | Mosier et al. |
| 2016/0281020 | A1 | 9/2016 | Yamamoto et al. |
| 2017/0015926 | A1 | 1/2017 | Fletcher et al. |
| 2017/0015930 | A1 | 1/2017 | Fletcher |
| 2017/0022441 | A1 | 1/2017 | Onodera |
| 2018/0002631 | A1 | 1/2018 | Milner |
| 2018/0112146 | A1 | 4/2018 | Moniz et al. |
| 2018/0237722 | A1 | 8/2018 | Burns, III et al. |
| 2019/0177651 | A1 | 6/2019 | Loper et al. |
| 2019/0284495 | A1 | 9/2019 | Abraham et al. |
| 2019/0367835 | A1 | 12/2019 | Ransom |
| 2020/0277541 | A1 * | 9/2020 | Meyke ................. C10M 135/10 |
| 2021/0371767 | A1 | 12/2021 | Shimizu et al. |

FOREIGN PATENT DOCUMENTS

| | | | | |
|---|---|---|---|---|
| EP | 0323087 | A1 | 7/1989 | |
| EP | 0612839 | A1 | 8/1994 | |
| EP | 1788068 | A1 | 5/2007 | |
| EP | 2639433 | A1 | 9/2013 | |
| EP | 3434755 | A1 | 1/2019 | |
| GB | 961009 | A | 6/1964 | |
| GB | 1162334 | A | 8/1969 | |
| JP | 2014152301 | A | 8/2014 | |
| JP | 2016534216 | A | 11/2016 | |
| JP | 2017514984 | A | 6/2017 | |
| JP | 2017149830 | A | 8/2017 | |
| JP | 201821107 | A | 2/2018 | |
| JP | 2018168344 | A | 11/2018 | |
| WO | WO-9714774 | A1 * | 4/1997 | ........... C07C 303/32 |
| WO | 2009104682 | A1 | 8/2009 | |
| WO | 2015023559 | A1 | 2/2015 | |
| WO | 2015042337 | A1 | 3/2015 | |
| WO | 2015042340 | A1 | 3/2015 | |
| WO | 2015042341 | A1 | 3/2015 | |
| WO | 2015076417 | A1 | 5/2015 | |
| WO | 20150114920 | A1 | 8/2015 | |
| WO | 2017011691 | A1 | 1/2017 | |
| WO | 2020085228 | A1 | 4/2020 | |
| WO | 2021158757 | A1 | 8/2021 | |

OTHER PUBLICATIONS

Haenel et al., Systematic Approach to Analyze and Characterize Pre-ignition Events in Turbocharged Direct-injected Gasoline Engines, SAE Int., Apr. 2011. (Abstract).

W. W. Yau, J. J. Kirkland and D. D. Bly, "Modern Size Exclusion Liquid Chromatography", John Wiley and Sons, New York, 1979.

Extended European Search Report for Application EP 24223269.2, dated May 28, 2025.

* cited by examiner

MAGNESIUM SULFONATE DETERGENT HAVING IMPROVED COMPATIBILITY WITH FRICTION MODIFIERS

TECHNICAL FIELD

The present disclosure generally relates to lubricating oil compositions and magnesium sulfonate detergents therefor having improved compatibility with friction modifiers.

BACKGROUND

Magnesium sulfonate is often used as a detergent in lubricating oil compositions for passenger cars and other vehicles. The detergents are often used in an overbased form, which is a compound having a stoichiometric excess of magnesium compared to the amount needed to neutralize the sulfonic acid. Prior overbased magnesium sulfonate detergents, however, tend to have compatibility issues, in some circumstances, with other additives commonly used in lubricants. For instance, overbased magnesium sulfonate detergents can have compatibility issues with common friction modifiers and, in particular, glycerol monooleate leading to dropouts, sediment, and/or film formation of the oil compositions. As such, when lubricating compositions including both overbased magnesium sulfonate and a friction modifier such as glycerol monooleate, one or both of the treat rates of such ingredients is often limited. As increased levels of friction modifiers are often desired for improved fuel economy, the compatibility issues of these two components tend to be a limiting factor in improving the performance of lubricating compositions.

SUMMARY

In accordance with one embodiment, a process for preparing an overbased magnesium sulfonate detergent having improved compatibility with friction modifiers is described herein. In one aspect, the process includes (a) preparing a mixture of a C14 to C24 alkylaryl sulfonic acid or salt thereof, magnesium oxide or magnesium hydroxide, and one or more branched C8 to C16 carboxylic acids; (b) carbonating the mixture to form an overbased magnesium sulfonate; and (c) treating the carbonated overbased magnesium sulfonate at about 160° C. to about 200° C. with about 6 to about 10 weight percent of a hydrocarbyl substituted succinic acid or anhydride. In aspects, the hydrocarbyl substituent of the hydrocarbyl substituted succinic acid or anhydride has a number average molecular weight of about 900 to about 1500 and derived from a polyisobutylene having greater than 50 mol percent of terminal double bonds, to form the overbased magnesium sulfonate detergent; and wherein the overbased magnesium sulfonate detergent has improved compatibility with friction modifiers.

In another approach or embodiment, the process described in the previous paragraph may include other features, steps, or embodiments in any combination. These other features, steps or embodiments may include one or more of the following: wherein the overbased magnesium sulfonate prior to the treating has a total base number (TBN) of at least about 450 mg KOH/g and the overbased magnesium sulfonate detergent after the treating has a total base number (TBN) of less than about 410 mg KOH/g; and/or wherein the overbased magnesium sulfonate detergent includes at least about 60 weight percent of magnesium sulfonate as an active ingredient; and/or wherein the overbased magnesium sulfonate detergent has about 35 weight percent or less of process oil; and/or wherein the treating step (c) is substantially free of dicarboxylic acids; and/or wherein the dicarbocylic acids are one or more of phthalic acid, succinic acid, maleic acid, azelaic acid, suberic acid, sebasic acid, fumaric acid, adipic acid, malonic acid, or combinations thereof, and/or wherein the overbased magnesium sulfonate is vacuum stripped at about 160° C. to about 200° C. prior to the treating step (c); and/or wherein the overbased magnesium sulfonate detergent is storage stable at about 55° C. when combined with up to about 0.4 weight percent of glycerol monooleate for at least about 18 weeks.

In yet another approach or embodiment, a storage-stable overbased magnesium sulfonate detergent having improved compatibility with friction modifiers is described herein. In one aspect, the storage-stable overbased magnesium sulfonate detergent is made by a process comprising: (a) preparing a mixture of a linear C14 to C24 alkylaryl sulfonic acid or salt thereof, magnesium oxide or magnesium hydroxide, and one or more branched C8 to C16 carboxylic acids; (b) carbonating the mixture to form an overbased magnesium sulfonate; and (c) treating the carbonated overbased magnesium sulfonate at about 160° C. to about 200° C. with about 6 to about 10 weight percent of a hydrocarbyl substituted succinic acid or anhydride. In other aspects, the hydrocarbyl substituent of the hydrocarbyl substituted succinic acid or anhydride has a number average molecular weight of about 900 to about 1500 and derived from a polyisobutylene having greater than 50 mol percent of terminal double bonds, to form the overbased magnesium sulfonate detergent; and wherein the overbased magnesium sulfonate detergent has improved compatibility with friction modifiers.

In further approaches, the storage-stable overbased magnesium sulfonate detergent of the previous paragraph includes other features or embodiments in any combination. These other features or embodiments include one or more of the following: wherein the overbased magnesium sulfonate prior to the treating has a total base number (TBN) of at least about 450 mg KOH/g and the overbased magnesium sulfonate detergent after the treating has a total base number (TBN) of less than about 410 mg KOH/g; and/or wherein the overbased magnesium sulfonate detergent includes at least about 60 weight percent of magnesium sulfonate as an active ingredient; and/or wherein the overbased magnesium sulfonate detergent has about 35 weight percent or less of process oil; and/or wherein the treating step (c) is substantially free of dicarboxylic acids; and/or wherein the dicarbocylic acids are one or more of phthalic acid, succinic acid, maleic acid, azelaic acid, suberic acid, sebasic acid, fumaric acid, adipic acid, malonic acid, or combinations thereof, and/or wherein the overbased magnesium sulfonate is vacuum stripped at about 160° C. to about 200° C. prior to the treating step (c); and/or wherein the overbased magnesium sulfonate detergent has a total base number (TBN) of about 350 to about 410 mg KOH/g and is storage stable at about 55° C. when combined with up to about 0.4 weight percent of glycerol monooleate friction modifier for at least about 18 weeks.

In yet another approach or embodiments, an engine oil lubricating composition is described herein including a major amount of one or more base oils of lubricating viscosity, any embodiment of the storage-stable overbased magnesium sulfonate detergent as described in this Summary (e.g., about 0.02 to about 5 weight percent or about 0.2 to about 2 weight percent), and up to about 0.4 weight percent of glycerol monooleate friction modifier.

In yet another approach or embodiment, a method of improving the storage stability of an overbased magnesium sulfonate detergent is described herein. In one aspect, the method included (a) preparing a mixture of a linear C14 to C24 alkylaryl sulfonic acid or salt thereof, magnesium oxide or magnesium hydroxide, and one or more branched C8 to C16 carboxylic acids; carbonating the mixture to form an overbased magnesium sulfonate; treating the formed overbased magnesium sulfonate at about 160° C. to about 200° C. with about 6 to about 10 weight percent of a hydrocarbyl substituted succinic anhydride, wherein the hydrocarbyl substituent thereof has a number average molecular weight of about 900 to about 1500 and derived from a polyisobutylene having greater than 50 mol percent of terminal double bonds, to form the overbased magnesium sulfonate detergent; and (b) combining about 0.02 to about 5 weight percent of the overbased magnesium sulfonate detergent with up to about 0.4 of glycerol monooleate friction modifier; and wherein the combination of the overbased magnesium sulfonate detergent and the glycerol monooleate friction modifier is storage stable at about 55° C. for at least about 18 weeks.

In other embodiments, the method of the previous paragraph may include other steps, features, or embodiments in any combination. These other steps, features, or embodiments include one or more of the following: wherein the overbased magnesium sulfonate prior to the treating has a total base number (TBN) of at least about 450 mg KOH/g and the overbased magnesium sulfonate detergent after the treating has a total base number (TBN) of less than about 410 mg KOH/g; and/or wherein the overbased magnesium sulfonate detergent includes at least about 60 weight percent of magnesium sulfonate as an active ingredient; and/or wherein the overbased magnesium sulfonate detergent has about 35 weight percent or less of process oil; and/or wherein the treating step (c) is substantially free of dicarboxylic acids; and/or wherein the dicarbocylic acids are one or more of phthalic acid, succinic acid, maleic acid, azelaic acid, suberic acid, sebasic acid, fumaric acid, adipic acid, malonic acid, or combinations thereof, and/or wherein the overbased magnesium sulfonate is vacuum stripped at about 160° C. to about 200° C. prior to the treating step (c); and/or wherein the overbased magnesium sulfonate detergent has a total base number (TBN) of about 350 to about 410 mg KOH/g and is storage stable at about 55° C. when combined with up to about 0.4 weight percent of glycerol monooleate friction modifier for at least about 18 weeks.

In yet other approaches or embodiments, the use of post treating an overbased magnesium sulfonate made via any of the approaches or embodiments of this Summary at about 160° C. to about 200° C. with about 6 to about 10 weight percent of a hydrocarbyl substituted succinic anhydride, and wherein the hydrocarbyl substituent thereof has a number average molecular weight of about 900 to about 1500 and derived from a polyisobutylene having greater than 50 mol percent of terminal double bonds, to form the overbased magnesium sulfonate detergent; and wherein the combination of the post-treated overbased magnesium sulfonate detergent (e.g., about 0.02 to about 5 weight percent) and glycerol monooleate friction modifier (up to about 0.4 weight percent) is storage stable at about 55° C. for at least about 18 weeks. The use may include any embodiment of this Summary.

Additional details and advantages of the disclosure will be set forth in part in the description that follows, and/or may be learned by practice of the disclosure. The details and advantages of the disclosure may be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure relates to improved overbased magnesium sulfonate detergents, methods of preparing the improved overbased magnesium sulfonate detergent, and methods of improving the storage stability of overbased magnesium sulfonate detergents. In one aspect, the methods and detergents herein produce an improved overbased magnesium sulfonate detergent having improved storage stability and/or compatibility with additives in lubricating oil compositions, and in particular, compatibility with friction modifiers such as glycerol monooleate conventionally used in automotive lubricating oil compositions.

In one embodiment, a process is described herein for preparing an improved overbased magnesium sulfonate detergent having enhanced compatibility with friction modifiers (such as glycerol monooleate). In one aspect, the process includes (a) preparing a reaction mixture of a C14 to C24 alkylaryl sulfonic acid or salt thereof, a magnesium compound, and one or more branched C8 to C16 carboxylic acids; (b) carbonating the reaction mixture to form an overbased magnesium sulfonate (the carbonation is combined with the reaction mixture or conducted after the reaction mixture is prepared); and (c) thereafter treating the carbonated overbased magnesium sulfonate at about 160° C. to about 200° C. with about 6 to about 10 weight percent of a hydrocarbyl substituted succinic acid or anhydride (in other approaches, about 6 to about 8 weight percent or about 8 to about 10 weight percent) and wherein the hydrocarbyl substituent thereof has a number average molecular weight of about 900 to about 1500 g/mol (in other approaches, about 900 to about 1200 g/mol) and derived from a polyisobutylene having greater than 50 mol percent of terminal double bonds. Such process forms the improved overbased magnesium sulfonate detergent. In another aspect, the improved overbased magnesium sulfonate detergent formed by such process has enhanced compatibility with friction modifiers such as glycerol monooleate and/or has enhanced storage stability as shown in the Examples herein.

Prior (e.g., not post treated as described herein) overbased detergents are well known in the art and may be alkali or alkaline earth metal overbased detergents. Such detergents may be prepared, for instance, by reacting a metal oxide or metal hydroxide with a substrate and an overbasing acid. The substrate is typically an acid, and in the case of sulfonate detergents, a substituted sulfonic acid (e.g., an alkylaryl sulfonic acid or sulfonate). The terminology "overbased" relates to the formed metal salts, such as metal salts in the form of sulfonates, wherein the amount of metal present exceeds the stoichiometric amount. Such salts may have a conversion level in excess of 100% (i.e., they may comprise more than 100% of the theoretical amount of metal needed to convert the acid substrate to its normal or "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR is greater than one. Such detergents are commonly referred to as overbased, hyperbased, or superbased salts and may be salts, in the case of sulfonate detergents, of organic sulfonic acids. As used herein, an overbased magnesium sulfonate detergent may have a TBN of greater 170 mg KOH/gram, a TBN of about 250 mg KOH/gram or greater, a TBN of about 300 mg KOH/gram or greater, or a TBN of about 350 mg KOH/gram or greater, or a TBN of about 375 mg KOH/gram or greater, or a TBN of about 400 mg KOH/gram or greater, or a TBN of about 400 to about 410 mg KOH/gram as measured by the method of ASTM D-2896. In other embodiments, the overbased magnesium sulfonate detergents herein have a TBN of about 175 to about 450 mg KOH/gram (or any other range therewith).

In one approach or embodiment, the improved overbased magnesium sulfonate detergents herein are prepared by post-treating a conventionally formed overbased magnesium sulfonate detergent with effective amounts of select hydrocarbyl substituted succinic acids or anhydrides and at conditions effective to improve the stability of the overbased magnesium sulfonate detergent. As discussed more below, it is preferred that the hydrocarbyl substituent of the succinic acid or anhydride post treat compound has a number average molecular weight of about 900 to about 1500 g/mol and derived from a polyisobutylene having greater than 50 mol percent of terminal double bonds (in other approaches, about 900 to about 1200 g/mol).

The starting conventionally-formed overbased magnesium sulfonate may be prepared by methods known in the art using either a one-step or a two-step process. In an exemplary two-step process, sulfonic acids or sulfonates (and preferably alkylaryl sulfonic acids or sulfonates) is first neutralized with a magnesium compound in a first step to produce a neutral magnesium sulfonate, and then through a second overbasing step with additional magnesium, as needed, and an overbasing acid, the overbased magnesium sulfonate is formed. Such two-step process may also include water, an optional promotor, base oil, and a hydrocarbon solvent as needed. The one-step process, in most instance, is generally preferred. In an exemplary one-step process, sulfonic acids or sulfonates (and preferably alkylaryl sulfonic acids or sulfonates) is combined with a molar excess of the magnesium compound, water, an optional promoter, base oil, and hydrocarbon solvent. The overbasing acid is then combined with this reaction mixture to form the overbased magnesium hydroxide in a single step process.

In one approach, the starting alkylaryl sulfonic acid or sulfonate may be derived from sulfonating an alkyl toluene or alkyl benzene, such as a linear or branched alkyl toluene or benzene, using various known sulfonating agents, such as, for example, sulfuric acid, sulfur trioxide, chlorosulfonic acid, or sulfamic acid. The alkylaryl sulfonic acid or alkylaryl sulphonate may be natural or synthetic with synthetic alkylaryl sulphonic acids and/or alkylaryl sulphonates being preferred. The alkyl substituent in such alkylaryl moieties may have 14 or more carbon atoms and, preferably, is a C14 to C24 linear or branched alkyl substituent. In one approach, the alkyl substituent is typically a polyolefin formed from an olefin having 2 to 5 carbon atoms, including ethylene, propylene, butylene, and/or pentylene monomers. In one approach, the alkyl substitution is an olefin, such as a normal alpha olefin that has from about 14 to about 24 carbon atoms. More preferably, the olefin is a normal alpha olefin that has from about 20 to about 24 carbon atoms. In other approaches, the alkyl substituent is a branched alkyl toluene or benzene and may be prepared by the alkylation of toluene with a branched-chain olefin. The branched chain olefin may be prepared the isomerization of a normal alpha olefin having at least 14 carbon atoms (and preferably 14 to 24 carbon atoms). The normal alpha olefin may be isomerized prior to, during, or after the alkylation step, but is preferably isomerized prior to the alkylation step. Methods of isomerizing olefins are known in the art. Preferably, the branched chain olefin is derived from the isomerization of normal alpha olefin that has from about 14 to about 24 carbon atoms. More preferably, the branched chain olefin is derived from the isomerization of a normal alpha olefin that has from about 20 to about 24 carbon atoms. The branched chain olefin may also be derived from an oligomer of propylene or butene comprising at least 9 carbon atoms, preferably from about 9 to 40 carbon atoms, more preferably from about 9 to 24 carbon atoms and most preferably from about 10 to 18 carbon atoms.

In embodiments, the magnesium compound provides the basicity to the overbased magnesium sulfonate and is present in a molar excess of the amount stoichiometrically required to react with the sulfonic acid. As noted above, the magnesium compound is often reacted in the presence of a hydrocarbon solvent and/or a low molecular weight alcohol. In one approach, the magnesium compound is magnesium oxide (MgO), magnesium hydroxide ($Mg(OH)_2$), or a magnesium alkoxide ($Mg(OR)_2$) wherein the alkoxide is derived from an alcohol having, for instance, 1 to 6 carbon atoms. Preferably, the magnesium compound is magnesium oxide or a mixture of magnesium oxide and magnesium hydroxide.

In some approaches, the process to form the conventional overbased magnesium sulfonate herein may also include a hydrocarbon solvent. Suitable hydrocarbon solvents may be n-pentane, n-hexane, cyclohexane, n-heptane, n-octane, isooctane, n-decane, benzene, toluene, xylene or mixtures thereof. Preferably, the hydrocarbon solvent is an aromatic solvent and is either xylene, benzene, toluene, or mixtures thereof, and most preferably, the solvent if used is xylene.

In approaches, the process to form the conventional overbased magnesium sulfonate herein may further include an optional low molecular weight alcohol. If used, the low molecular weight alcohol must have a boiling point sufficiently low so that it may be easily distilled off after the reaction has occurred. Typically, the low molecular weight alcohol will have from about 1 to about 13 carbon atoms and a molecular weight no higher than about 200. In one embodiment, the low molecular weight alcohol is a low molecular weight monohydric alcohol. In a more preferred embodiment, the low molecular weight monohydric alcohol may be selected from the group consisting of $C_1$ to $C_{13}$ alcohols and glycol monoethers and monoesters. Preferably, the low molecular weight alcohol is a monohydric alcohol selected from the group consisting of methanol, ethanol, propanol, isooctanol, cyclohexanol, cyclopentanol, isobutyl alcohol, benzyl alcohol, beta-phenyl-ethyl alcohol, 2-ethylhexanol, dodecanol, tridecanol, 2-methylcyclohexanol, monomethyl ether of ethylene glycol, monobutyl ether of ethylene glycol, sec-pentyl alcohol, and tert-butyl alcohol. The most preferred low molecular weight monohydric alcohol is methanol (which may be added as a promotor).

The process to form a conventional overbased magnesium sulfonate may include a promoter or co-promotor. The promotor tends to improve the acid-base contact to facilitate the neutralization and subsequent overbasing reaction. If used, the promoter or co-promotor is preferably one or more monocarboxylic acids. Suitable monocarboxylic acids have from 1 to 24 carbon atoms and, preferably, 8 to 16 carbon atoms, and most preferably a branched 8 to 16 carbon chain. The monocarboxylic acids may be aliphatic or aromatic, saturated or unsaturated, and suitable monocarboxylic acids include formic acid, acetic acid, stearic acid, benzoic acid, salicylic acid, neodecanoic acid, or mixtures thereof. Preferably, the promotor or co-promotor is a branched C8 to C16 carboxylic acid, and most preferably, the promotor or co-promoter is neodecanoic acid.

In approaches or embodiments herein, the process to form the conventional overbased magnesium sulfonate detergents herein is substantially free of, and preferably free of any promotor or co-promotor derived from or based on a hydrocarbyl-substituted succinic acid, anhydride or derivative thereof. For instance, the processes herein are substantially free of and preferably free of any promotor or co-promotor of a dodecenyl succinic acid or anhydride, an octadecenyl succinic acid or anhydride, and/or a polyisobutylene succinic acid or anhydride based promotors. As used herein, "substantially free of" means the reaction mixtures to form the conventional overbased magnesium sulfonate include less than about 1 weight percent, preferably less than about 0.5 weight percent, and more preferably, less than about 0.1 weight percent of hydrocarbyl-substituted succinic acid, anhydride or derivative based promotors or co-promotors. As also used herein, "free of" means the reaction mixtures to form the conventional overbased magnesium sulfonates include no detectable amounts of the hydrocarbyl-substituted succinic acid, anhydride or derivative based promotors or co-promotors. As discussed more below, certain hydrocarbyl-substituted succinic acids or anhydrides are used in a post treatment, but such post-treat addition is distinct from the previously used promotors or co-promoters used during the overbasing.

In approaches, the overbasing acid used to form the conventional overbased magnesium sulfonate is any acid capable of providing an oil-soluble magnesium sulfonate with greater than a stoichiometric amount of magnesium relative to the alkylaryl sulfonic acid or salt thereof. The most common overbasing acid is carbon dioxide, but other overbasing acids may include sulfur dioxide and/or sulfur trioxide. The acid itself may be part of the overbasing process, or alternatively a source of an overbasing acid such as ethylene carbonate may be used to introduce the overbasing acid. The most preferred acid is carbon dioxide and the one-step or two-step process using the overbasing acid typically refers to such component as carbonation no matter what overbasing acid may be used An exemplary reaction scheme to form the starting conventional overbased magnesium sulfonate is provided by Reaction Scheme I below with $R_1$ being hydrogen or a $C_1$ to $C_4$ hydrocarbyl group (preferably a methyl group) and $R_2$ being a linear or branched C14 to C24 hydrocarbyl group. The starting conventional overbased magnesium sulfonate has a total base number (TBN) of greater 170 mg KOH/gram, or as further examples, a TBN of about 250 mg KOH/gram or greater, a TBN of about 300 mg KOH/gram or greater, or a TBN of about 350 mg KOH/gram or greater, or a TBN of about 375 mg KOH/gram or greater, or a TBN of about 400 mg KOH/gram or greater, or a TBN of about 400 to about 450 mg KOH/gram or greater as measured by the method of ASTM D-2896.

(Reaction Scheme I)

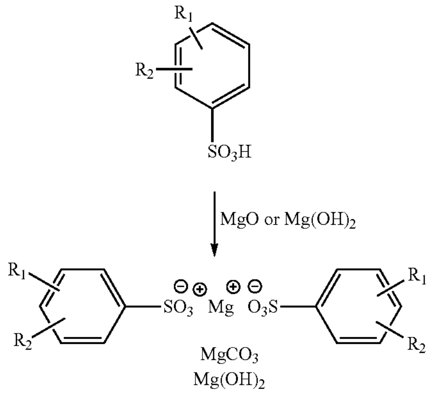

This conventionally-formed overbased magnesium sulfonate from Reaction Scheme I may also be subjected to a number of optional post processing steps (which are distinct from the post-treatment steps described further below). Suitable post-processing steps may include one or more of vacuum stripping, distillation, sparging, filtering, degassing, evaporation, wiped-film evaporating, centrifuging, diluting, liquid-liquid extraction, membrane separation, chromatography, absorption, supercritical extractions, and/or combinations thereof and wherein all post processing individually and/or combined is generally conducted at a temperature of about 160° C. to about 200° C. Any of such optional post-processing steps is conducted before the post-treating steps described more below with the select hydrocarbyl-substituted succinic acid or anhydride.

As shown in the Examples, such conventionally-formed overbased magnesium sulfonate tends to be incompatible with commonly used friction modifiers in lubricating oil compositions, and in particular, glycerol monooleate. When such conventional overbased magnesium sulfonate is combined with glycerol monoleate in a lubricating oil composition, it tends to have limited storage stability of no more than 7 to 10 weeks at about 55° C. before forming dropouts, sediment, and/or film. While not wishing to be limited by theory, it is believed that the inorganic magnesium core of the conventional overbased magnesium sulfonate is capable of interacting with various moieties of the friction modifiers and, in particular, moieties of the glycerol monooleate resulting in the instability of the compositions and the detergent thereof.

Post-Treatment

To improve the storage stability of the conventionally formed overbased magnesium sulfonate detergents, the conventional overbased magnesium detergent is post treated with selected amounts of and under select conditions of a post-treat reactant including a hydrocarbyl-substituted succinic acid or anhydride and, preferably, a hydrocarbyl-substituted succinic acid or anhydride having a hydrocarbyl substituent of a polyisobutylene with a number average molecular weight of about 900 to about 1500 g/mol (in other approaches, about 900 to about 1200 g/mol, about 900 to about 1100 g/mol, or about 950 to about 1000 g/mol) and derived from a polyisobutylene having greater than 50 mol percent of terminal double bonds as described more below.

In embodiments, the post treatment occurs at a temperature of about 160° C. to about 200° C. (in other approaches, 170° C. to about 185° C., and in further approaches, 175° C. to about 185° C., and most preferably about 180° C.) and with about 6 to about 10 weight percent of the hydrocarbyl-substituted succinic acid or anhydride (in other approaches, about 6 to about 8 weight percent or about 8 to about 10 weight percent.) The post-treatment is for about 15 minutes to about 60 minutes and thereafter the mixture is cooled to about 70 to about 80° C. The post-treatment mixture is typically about 60 to about 70 weight percent of the overbased magnesium sulfonate (active basis), about 25 to about 35 weight percent of process oil, and effective amounts of the selected hydrocarbyl-substituted succinic acid or anhydride. Thus in embodiments herein, the formed improved overbased magnesium sulfonate detergent made by the processes herein is a detergent or detergent composition including about 60 to about 70 weight percent of the overbased magnesium sulfonate (active basis), about 25 to about 35 weight percent of process oil, and about 6 to about 10 weight percent (or about 6 to about 8 weight percent or about 8 to about 10 weight percent) of the selected hydrocarbyl substituted succinic acid or anhydride.

Before post-treatment, the TBN of the overbased magnesium sulfonate detergent is often about 400 mg or KOH/gram or higher and, in some cases about 450 mg of KOH/gram or higher (preferably, greater than 410 to about 470 or about 420 to about 460), and after the post-treatment, the TBN of the improved overbased magnesium sulfonate detergent is usually about 375 to about 410 mg KOH/gram (preferably, about 400 to about 410 mg KOH/gram) or other TBN values as noted herein for an overbased detergent. After the post-treating, the KV100 of the post-treated overbased magnesium detergent including the detergent, process oil, and hydrocarbyl-substituted succinic acid or anhydride is about 100 to about 200 cSt (ASTM D425), about 125 to about 175 cSt, or about 140 to about 160 cSt. As shown in the Examples below, such improved overbased magnesium sulfonate detergent is storage stable at about 55° C. when combined with up to about 0.4 weight percent of glycerol monooleate for at least about 18 weeks, at least about 20 weeks, at least about 24 weeks, or longer.

In some embodiment, the post-treatment step is substantially free of, and preferably free-of dicarboxylic acids. For example, the post-treatment steps of the processes herein using the selected dicarboxylic acids are preferably substantially free of or free-of dicarboxylic acids including one or more of phthalic acid, succinic acid, maleic acid, azelaic acid, suberic acid, sebasic acid, fumaric acid, adipic acid, malonic acid, or combinations thereof. As used herein, "substantially free of" in the context of dicarboxylic acids during the post-treatment means the post-treatment include less than about 1 weight percent, preferably less than about 0.5 weight percent, and more preferably, less than about 0.1 weight percent of dicarboxylic acid. As also used herein, "free of" in the context of dicarboxylic acids during the post-treatment means no detectable amounts of any dicarboxylic acid.

Post-Treating Agent: The post-treating agent is a select hydrocarbyl-substituted succinic acid or anhydride. The select hydrocarbyl-substituted succinic acid or anhydride may be prepared as known in the art by reacting an olefinically unsaturated hydrocarbon of the noted molecular weight with maleic acid or maleic anhydride (or the like as discussed below) to form the hydrocarbyl-substituted succinic aid or anhydride. Reaction temperatures of about 100° C. to about 250° C. may be used. This reaction is often promoted by the addition of chlorine.

The selected hydrocarbyl substituent may include olefins such as, but are not limited to, cracked wax olefins, linear alpha olefins, branched chain alpha olefins, polymers and copolymers of lower olefins. The olefins can be chosen from ethylene, propylene, butylene, such as isobutylene, 1-octane, 1-hexene, 1-decene and the like. Some useful polymers and/or copolymers of lower olefins include, but are not limited to, polypropylene, polybutenes, polyisobutene, ethylene-propylene copolymers, ethylene-isobutylene copolymers, propylene-isobutylene copolymers, ethylene-1-decene copolymers and the like. Hydrocarbyl substituents have also been made from olefin terpolymers. Useful products can be made from ethylene-$C_{3-12}$ alpha olefin-$C_{5-12}$ non-conjugated diene terpolymers; such as ethylene-propylene-1,4-hexadiene terpolymer; ethylenepropylene-1,5-cyclooctadiene terpolymer; ethylene-propylenenorbornene terpolymers and the like.

The number average molecular weight of the selected hydrocarbyl substituent for the post-treat reactants herein is limited to about 900 to about 1500 g/mol, in other approaches, about 900 to about 1200 g/mol, and in other approaches, about 950 to about 1100 g/mol, or about 950 to about 1000 g/mol, as determined by gel permeation chromatography (GPC) using polystyrene as a calibration reference as described herein. As shown in the Examples below, lower and higher molecular weights of the hydrocarbyl substituent unexpectedly degrade the stability when the resultant overbased magnesium sulfonate (even when post-treated) is combined with the friction modifiers.

Carboxylic reactants other than maleic acid or maleic anhydride can also be employed in some approaches to form the polycarboxylic acid or anhydrides herein. Suitable reactants may also include, but not be limited to, fumaric acid, malic acid, tartaric acid, itaconic acid, itaconic anhydride, citraconic acid, citraconic anhydride, mesaconic acid, ethylmaleic anhydride, dimethylmaleic anhydride, ethylmaleic acid, dimethylmaleic acid, hexylmaleic acid, and the like, including the corresponding acid halides and lower aliphatic esters.

In some embodiments, the selected hydrocarbyl-substituted succinic anhydrides or acids may be prepared by the thermal reaction of the polyolefin and maleic anhydride, as described, for example in U.S. Pat. Nos. 3,361,673 and 3,676,089, the disclosures of which are incorporated by reference. Alternatively, the substituted succinic anhydrides can be prepared by the reaction of chlorinated polyolefins with maleic anhydride, as described, for example, in U.S. Pat. No. 3,172,892, the disclosure of which is also incorporated by reference. A further discussion of hydrocarbyl-substituted succinic anhydrides can be found, for example, in U.S. Pat. Nos. 4,234,435; 5,620,486 and 5,393,309, the disclosures of which are incorporated by reference.

In some approaches, a mole ratio of maleic anhydride (or other acylating agent) to the olefinic unsaturated hydrocarbon can vary widely. For example, it can vary from about 5:1 to about 1:5, in other approaches, from about 3:1 to about 1:3, and in yet other approaches, the maleic anhydride can be used in stoichiometric excess to force the reaction to completion. If needed, the unreacted maleic anhydride can be removed by vacuum distillation In preferred embodiments, the hydrocarbyl substituent used to form the post-treat reactants herein is derived from polyisobutylene (PIB), and most preferably polyisobutylene having greater than 50 mol %, greater than 60 mol %, greater than 70 mol %, greater than 80 mol %, or greater than 90 mol % content of terminal double bonds. Such PIB is referred to as highly reactive PIB ("HR-PIB"). HR-PIB having a number average molecular weight ranging from about 900 to about 1500, as determined by GPC, is most suitable for use in embodiments of the present disclosure. Conventional PIB typically has less than 50 mol %, less than 40 mol %, less than 30 mol %, less than 20 mol %, or less than 10 mol % content of terminal double bonds. Such HR-PIB is commercially available, or can be synthesized by the polymerization of isobutene in the presence of a non-chlorinated catalyst such as boron trifluoride, as described in U.S. Pat. Nos. 4,152,499 and/or 5,739,355, which are both incorporated herein by reference.

Lubricating Oil Compositions

The improved overbased magnesium sulfonate detergent herein may be combined with a major amount of a base oil blend or base oil blend of lubricating viscosity (as described below) in combination with one or more further optional additives to produce a lubricating oil composition. In approaches, the lubricating oil compositions includes about 50 weight percent or more of the base oil, about 60 weight percent or more, about 70 weight percent or more, or about 80 weight percent or more to about 95 weight percent or less, about 90 weight percent or less, about 85 weight percent or less of the base oil as further discussed below.

In approaches, the lubricating oil compositions herein may include about 0.02 to about 5 weight percent of the improved overbased magnesium sulfonate detergent, in other approaches, about 0.2 to about 3 weight percent, and in yet other approaches, about 0.2 to about 2 weight percent in a base oil or base oil blend. As shown in the Examples below, the lubricating oil compositions may also include up to about 0.4 weight percent of a friction modifier and, in particular, glycerol monooleate and remain storage stable. Such combinations of additives (e.g., improved overbased magnesium sulfonate detergent and glycerol monooleate) are storage stabile (e.g., free of sediment, dropout, and/or film formation) for at least about 18 weeks at about 55° C. As used herein, storage stable means free of any sediment or film at the bottom of a 20 to 20 gram sample in a clear glass vial and when viewed with the presence of a backlight.

Lubricants, combinations of components, dispersant inhibitor packages, and/or individual components of the present description may be suitable for use in various types of lubricants such as automotive lubricants and/or greases, internal combustion engine oils, hybrid engine oils, hybrid engine oils, electric engine lubricants, drivetrain lubricants, transmission lubricants, gear oils, hydraulic lubricants, tractor hydraulic fluids, metalworking fluids, turbine engine lubricants, stationary engine lubricants, tractor lubricants, motorcycle lubricants, power steering fluids, clutch fluids, axle fluids, wet break fluids, and the like.

Suitable engine types may include, but are not limited to heavy-duty diesel, passenger car, light duty diesel, medium speed diesel, or marine engines. An internal combustion engine may be a diesel fueled engine, a gasoline fueled engine, a natural gas fueled engine, a bio-fueled engine, a mixed diesel/biofuel fueled engine, a mixed gasoline/biofuel fueled engine, an alcohol fueled engine, a mixed gasoline/alcohol fueled engine, a compressed natural gas (CNG) fueled engine, or mixtures thereof. A diesel engine may be a compression-ignited engine. A gasoline engine may be a spark-ignited engine. An internal combustion engine may also be used in combination with an electrical or battery source of power. An engine so configured is commonly known as a hybrid engine. The internal combustion engine may be a 2-stroke, 4-stroke, or rotary engine. Suitable internal combustion engines include marine diesel engines (such as inland marine), aviation piston engines, low-load diesel engines, and motorcycle, automobile, locomotive, and truck engines. Engines may be coupled with a turbocharger.

The lubricating oil composition for an internal combustion engine may be suitable for any engine lubricant irrespective of the sulfur, phosphorus, or sulfated ash (ASTM D-874) content. The sulfur content of the engine oil lubricant may be about 1 wt % or less, or about 0.8 wt % or less, or about 0.5 wt % or less, or about 0.3 wt % or less, or about 0.2 wt % or less. In one embodiment the sulfur content may be in the range of about 0.001 wt % to about 0.5 wt %, or about 0.01 wt % to about 0.3 wt %. The phosphorus content may be about 0.2 wt % or less, or about 0.1 wt % or less, or about 0.085 wt % or less, or about 0.08 wt % or less, or even about 0.06 wt % or less, about 0.055 wt % or less, or about 0.05 wt % or less. In one embodiment, the phosphorus content may be about 50 ppm to about 1000 ppm, or about 325 ppm to about 850 ppm. The total sulfated ash content may be about 2 wt % or less, or about 1.5 wt % or less, or about 1.1 wt % or less, or about 1 wt % or less, or about 0.8 wt % or less, or about 0.5 wt % or less. In one embodiment the sulfated ash content may be about 0.05 wt % to about 0.9 wt %, or about 0.1 wt % or about 0.2 wt % to about 0.45 wt %. In another embodiment, the sulfur content may be about 0.4 wt % or less, the phosphorus content may be about 0.08 wt % or less, and the sulfated ash is about 1 wt % or less. In yet another embodiment the sulfur content may be about 0.3 wt % or less, the phosphorus content is about 0.05 wt % or less, and the sulfated ash may be about 0.8 wt % or less.

Further, lubricants of the present description may be suitable to meet one or more industry specification requirements such as ILSAC GF-3, GF-4, GF-5, GF-6, PC-11, CF, CF-4, CH-4, CK-4, FA-4, CJ-4, CI-4 Plus, CI-4, API SG, SJ, SL, SM, SN, SN PLUS, ACEA A1/B1, A2/B2, A3/B3, A3/B4, A5/B5, C1, C2, C3, C4, C5, E4/E6/E7/E9, Euro 5/6, JASO DL-1, Low SAPS, Mid SAPS, or original equipment manufacturer specifications such as Dexos1™, Dexos2™, MB-Approval 229.1, 229.3, 229.5, 229.51/229.31, 229.52, 229.6, 229.71, 226.5, 226.51, 228.0/.1, 228.2/.3, 228.31, 228.5, 228.51, 228.61, VW 501.01, 502.00, 503.00/503.01, 504.00, 505.00, 505.01, 506.00/506.01, 507.00, 508.00, 509.00, 508.88, 509.99, BMW Longlife-01, Longlife-01 FE, Longlife-04, Longlife-12 FE, Longlife-14 FE+, Longlife-17 FE+, Porsche A40, C30, Peugeot Citroen Automobiles B71 2290, B71 2294, B71 2295, B71 2296, B71 2297, B71 2300, B71 2302, B71 2312, B71 2007, B71 2008, Renault RN0700, RN0710, RN0720, Ford WSS-M2C153-H, WSS-M2C930-A, WSS-M2C945-A, WSS-M2C913A, WSS-M2C913-B, WSS-M2C913-C, WSS-M2C913-D, WSS-M2C948-B, WSS-M2C948-A, GM 6094-M, Chrysler MS-6395, Fiat 9.55535 G1, G2, M2, N1, N2, Z2, S1, S2, S3, S4, T2, DS1, DSX, GH2, GS1, GSX, CR1, Jaguar Land Rover STJLR.03.5003, STJLR.03.5004, STJLR.03.5005, STJLR.03.5006, STJLR.03.5007, STJLR.51.5122 or any past or future PCMO or HDD specifications not mentioned herein. In some embodiments for passenger car motor oil (PCMO) applications, the amount of phosphorus in the finished fluid is 1000 ppm or less or 900 ppm or less or 800 ppm or less.

Base Oil or Base Oil Blend: The base oil used in the lubricating oil compositions herein may be oils of lubricating viscosity and selected from any of the base oils in Groups I-V as specified in the American Petroleum Institute (API) Base Oil Interchangeability Guidelines. The five base oil groups are generally set forth in Table 1 below:

TABLE 1

| Base oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | All polyalpha-olefins (PAOs) | | | |
| Group V | All others not included in Groups I, II, III, or IV | | | |

Groups I, IL, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may be referred to as synthetic fluids in the industry. Group II+ may comprise high viscosity index Group II.

The base oil blend used in the disclosed lubricating oil composition may be a mineral oil, animal oil, vegetable oil, synthetic oil, synthetic oil blends, or mixtures thereof. Suitable oils may be derived from hydrocracking, hydrogenation, hydrofinishing, unrefined, refined, and re-refined oils, and mixtures thereof.

Unrefined oils are those derived from a natural, mineral, or synthetic source without or with little further purification treatment. Refined oils are similar to the unrefined oils except that they have been treated in one or more purification steps, which may result in the improvement of one or more properties. Examples of suitable purification techniques are solvent extraction, secondary distillation, acid or base extraction, filtration, percolation, and the like. Oils refined to the quality of an edible may or may not be useful. Edible oils may also be called white oils. In some embodiments, lubricating oil compositions are free of edible or white oils.

Re-refined oils are also known as reclaimed or reprocessed oils. These oils are obtained similarly to refined oils using the same or similar processes. Often these oils are additionally processed by techniques directed to removal of spent additives and oil breakdown products.

Mineral oils may include oils obtained by drilling or from plants and animals or any mixtures thereof. For example such oils may include, but are not limited to, castor oil, lard oil, olive oil, peanut oil, corn oil, soybean oil, and linseed oil, as well as mineral lubricating oils, such as liquid petroleum oils and solvent-treated or acid-treated mineral lubricating oils of the paraffinic, naphthenic or mixed paraffinic-naphthenic types. Such oils may be partially or fully hydrogenated, if desired. Oils derived from coal or shale may also be useful.

Useful synthetic lubricating oils may include hydrocarbon oils such as polymerized, oligomerized, or interpolymerized olefins (e.g., polybutylenes, polypropylenes, propyleneisobutylene copolymers); poly(1-hexenes), poly(1-octenes), trimers or oligomers of 1-decene, e.g., poly(1-decenes), such materials being often referred to as α-olefins, and mixtures thereof, alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulfides and the derivatives, analogs and homologs thereof or mixtures thereof. Polyalphaolefins are typically hydrogenated materials.

Other synthetic lubricating oils include polyol esters, diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerized Fischer-Tropsch hydrocarbons or waxes. In one embodiment oils may be prepared by a Fischer-Tropsch gas-to-liquid synthetic procedure as well as other gas-to-liquid oils.

The major amount of base oil included in a lubricating composition may be selected from the group consisting of Group I, Group II, a Group III, a Group IV, a Group V, and a combination of two or more of the foregoing, and wherein the major amount of base oil is other than base oils that arise from provision of additive components or viscosity index improvers in the composition. In another embodiment, the major amount of base oil included in a lubricating composition may be selected from the group consisting of Group II, a Group III, a Group IV, a Group V, and a combination of two or more of the foregoing, and wherein the major amount of base oil is other than base oils that arise from provision of additive components or viscosity index improvers in the composition.

The amount of the oil of lubricating viscosity present may be the balance remaining after subtracting from 100 wt % the sum of the amount of the performance additives inclusive of viscosity index improver(s) and/or pour point depressant(s) and/or other top treat additives. For example, the oil of lubricating viscosity that may be present in a finished fluid may be a major amount, such as greater than about 50 wt %, greater than about 60 wt %, greater than about 70 wt %, greater than about 80 wt %, greater than about 85 wt %, or greater than about 90 wt %.

Optional Additives:

The lubricating oil compositions herein may also include a number of optional additives combined with the optionally overbased and sulfurized alkyl phenate product as needed to meet performance standards. Those optional additives are described in the following paragraphs.

Dispersants: The lubricating oil composition may optionally include one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless type dispersants are characterized by a polar group attached to a relatively high molecular weight hydrocarbon chain. Typical ashless dispersants include N-substituted long chain alkenyl succinimides. Examples of N-substituted long chain alkenyl succinimides include polyisobutylene succinimide with the number average molecular weight of the polyisobutylene substituent being in the range about 350 to about 50,000, or to about 5,000, or to about 3,000, as measured by GPC. Succinimide dispersants and their preparation are disclosed, for instance in U.S. Pat. No. 7,897,696 or U.S. Pat. No. 4,234,435. The alkenyl substituent may be prepared from polymerizable monomers containing about 2 to about 16, or about 2 to about 8, or about 2 to about 6 carbon atoms. Succinimide dispersants are typically the imide formed from a polyamine, typically a poly(ethyleneamine).

Preferred amines are selected from polyamines and hydroxyamines. Examples of polyamines that may be used include, but are not limited to, diethylene triamine (DETA), triethylene tetramine (TETA), tetraethylene pentamine (TEPA), and higher homologues such as pentaethylamine hexamine (PEHA), and the like.

A suitable heavy polyamine is a mixture of polyalkylene-polyamines comprising small amounts of lower polyamine oligomers such as TEPA and PEHA (pentaethylene hexamine) but primarily oligomers with 6 or more nitrogen atoms, 2 or more primary amines per molecule, and more extensive branching than conventional polyamine mixtures. A heavy polyamine preferably includes polyamine oligomers containing 7 or more nitrogens per molecule and with 2 or more primary amines per molecule. The heavy polyamine comprises more than 28 wt. % (e.g. >32 wt. %) total nitrogen and an equivalent weight of primary amine groups of 120-160 grams per equivalent.

In some approaches, suitable polyamines are commonly known as PAM and contain a mixture of ethylene amines where TEPA and pentaethylene hexamine (PEHA) are the major part of the polyamine, usually less than about 80%.

Typically, PAM has 8.7-8.9 milliequivalents of primary amine per gram (an equivalent weight of 115 to 112 grams per equivalent of primary amine) and a total nitrogen content of about 33-34 wt. %. Heavier cuts of PAM oligomers with practically no TEPA and only very small amounts of PEHA but containing primarily oligomers with more than 6 nitrogens and more extensive branching, may produce dispersants with improved dispersancy.

In an embodiment the present disclosure further comprises at least one polyisobutylene succinimide dispersant derived from polyisobutylene with a number average molecular weight in the range about 350 to about 50,000, or to about 5000, or to about 3000, as determined by GPC. The polyisobutylene succinimide may be used alone or in combination with other dispersants.

In some embodiments, polyisobutylene, when included, may have greater than 50 mol %, greater than 60 mol %, greater than 70 mol %, greater than 80 mol %, or greater than 90 mol % content of terminal double bonds. Such PIB is also referred to as highly reactive PIB ("HR-PIB"). HR-PIB having a number average molecular weight ranging from about 800 to about 5000, as determined by GPC, is suitable for use in embodiments of the present disclosure. Conventional PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable, as determined by GPC. Such HR-PIB is commercially available, or can be synthesized by the polymerization of isobutene in the presence of a non-chlorinated catalyst such as boron trifluoride, as described in U.S. Pat. No. 4,152,499 to Boerzel, et al. and U.S. Pat. No. 5,739,355 to Gateau, et al. When used in the aforementioned thermal ene reaction, HR-PIB may lead to higher conversion rates in the reaction, as well as lower amounts of sediment formation, due to increased reactivity. A suitable method is described in U.S. Pat. No. 7,897,696.

In one embodiment, the present disclosure further comprises at least one dispersant derived from polyisobutylene succinic anhydride ("PIBSA"). The PIBSA may have an average of between about 1.0 and about 2.0 succinic acid moieties per polymer.

The % actives of the alkenyl or alkyl succinic anhydride can be determined using a chromatographic technique. This method is described in column 5 and 6 in U.S. Pat. No. 5,334,321.

The percent conversion of the polyolefin is calculated from the % actives using the equation in column 5 and 6 in U.S. Pat. No. 5,334,321.

Unless stated otherwise, all percentages are in weight percent and all molecular weights are number average molecular weights determined by gel permeation chromatography (GPC) using commercially available polystyrene standards (with a number average molecular weight of 180 to about 18,000 as the calibration reference).

In one embodiment, the dispersant may be derived from a polyalphaolefin (PAO) succinic anhydride. In one embodiment, the dispersant may be derived from olefin maleic anhydride copolymer. As an example, the dispersant may be described as a poly-PIBSA. In an embodiment, the dispersant may be derived from an anhydride which is grafted to an ethylene-propylene copolymer.

A suitable class of nitrogen-containing dispersants may be derived from olefin copolymers (OCP), more specifically, ethylene-propylene dispersants which may be grafted with maleic anhydride. A more complete list of nitrogen-containing compounds that can be reacted with the functionalized OCP are described in U.S. Pat. Nos. 7,485,603; 7,786,057; 7,253,231; 6,107,257; and 5,075,383; and/or are commercially available.

One class of suitable dispersants may also be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may also be high molecular weight esters or half ester amides. A suitable dispersant may also be post-treated by conventional methods by a reaction with any of a variety of agents. Among these are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. Nos. 7,645,726; 7,214,649; and 8,048,831 are incorporated herein by reference in their entireties.

In addition to the carbonate and boric acids post-treatments both the compounds may be post-treated, or further post-treatment, with a variety of post-treatments designed to improve or impart different properties. Such post-treatments include those summarized in columns 27-29 of U.S. Pat. No. 5,241,003, hereby incorporated by reference. Such treatments include, treatment with: Inorganic phosphorous acids or anhydrates (e.g., U.S. Pat. Nos. 3,403,102 and 4,648,980); Organic phosphorous compounds (e.g., U.S. Pat. No. 3,502,677); Phosphorous pentasulfides; Boron compounds as already noted above (e.g., U.S. Pat. Nos. 3,178,663 and 4,652,387); Carboxylic acid, polycarboxylic acids, anhydrides and/or acid halides (e.g., U.S. Pat. Nos. 3,708,522 and 4,948,386); Epoxides polyepoxiates or thioexpoxides (e.g., U.S. Pat. Nos. 3,859,318 and 5,026,495); Aldehyde or ketone (e.g., U.S. Pat. No. 3,458,530); Carbon disulfide (e.g., U.S. Pat. No. 3,256,185); Glycidol (e.g., U.S. Pat. No. 4,617,137); Urea, thiourea or guanidine (e.g., U.S. Pat. Nos. 3,312,619; 3,865,813; and British Patent GB 1,065,595);

Organic sulfonic acid (e.g., U.S. Pat. No. 3,189,544 and British Patent GB 2,140,811); Alkenyl cyanide (e.g., U.S. Pat. Nos. 3,278,550 and 3,366,569); Diketene (e.g., U.S. Pat. No. 3,546,243); A diisocyanate (e.g., U.S. Pat. No. 3,573,205); Alkane sultone (e.g., U.S. Pat. No. 3,749,695); 1,3-Dicarbonyl Compound (e.g., U.S. Pat. No. 4,579,675); Sulfate of alkoxylated alcohol or phenol (e.g., U.S. Pat. No. 3,954,639); Cyclic lactone (e.g., U.S. Pat. Nos. 4,617,138; 4,645,515; 4,668,246; 4,963,275; and 4,971,711); Cyclic carbonate or thiocarbonate linear monocarbonate or polycarbonate, or chloroformate (e.g., U.S. Pat. Nos. 4,612,132; 4,647,390; 4,648,886; 4,670,170); Nitrogen-containing carboxylic acid (e.g., U.S. Pat. No. 4,971,598 and British Patent GB 2,140,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603 and 4,666,460); Cyclic carbonate or thiocarbonate, linear monocarbonate or polycarbonate, or chloroformate (e.g., U.S. Pat. Nos. 4,612,132; 4,647,390; 4,646,860; and 4,670,170); Nitrogen-containing carboxylic acid (e.g., U.S. Pat. No. 4,971,598 and British Patent GB 2,440,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603, and 4,666,460); Cyclic carbamate, cyclic thiocarbamate or cyclic dithiocarbamate (e.g., U.S. Pat. Nos. 4,663,062 and 4,666,459); Hydroxyaliphatic carboxylic acid (e.g., U.S. Pat. Nos. 4,482,464; 4,521,318; 4,713,189); Oxidizing agent (e.g., U.S. Pat. No. 4,379,064); Combination of phosphorus pentasulfide and a polyalkylene polyamine (e.g., U.S. Pat. No. 3,185,647); Combination of carboxylic acid or an aldehyde or ketone and sulfur or sulfur chloride (e.g., U.S. Pat. Nos. 3,390,086; 3,470,098); Combination of a hydrazine and carbon disulfide (e.g. U.S. Pat. No. 3,519,564); Combination of an aldehyde and a phenol (e.g., U.S. Pat. Nos. 3,649,229; 5,030,249; 5,039,307); Combination of an aldehyde and an O-diester of dithiophosphoric acid (e.g., U.S. Pat. No. 3,865,740); Combination of a hydroxyaliphatic carboxylic acid and a boric acid (e.g., U.S. Pat. No. 4,554,086); Combination of a hydroxyaliphatic carboxylic acid, then formaldehyde and a phenol (e.g., U.S. Pat. No. 4,636,322); Combination of a hydroxyaliphatic carboxylic acid and then an aliphatic dicarboxylic acid (e.g., U.S. Pat. No. 4,663,064); Combination of formaldehyde and a phenol and then glycolic acid (e.g., U.S. Pat. No. 4,699,724); Combination of a hydroxyaliphatic carboxylic acid or oxalic acid and then a diisocyanate (e.g. U.S. Pat. No. 4,713,191); Combination of inorganic acid or anhydride of phosphorus or a partial or total sulfur analog thereof and a boron compound (e.g., U.S. Pat. No. 4,857,214); Combination of an organic diacid then an unsaturated fatty acid and then a nitrosoaromatic amine optionally followed by a boron compound and then a glycolating agent (e.g., U.S. Pat. No. 4,973,412); Combination of an aldehyde and a triazole (e.g., U.S. Pat. No. 4,963,278); Combination of an aldehyde and a triazole then a boron compound (e.g., U.S. Pat. No. 4,981,492); Combination of cyclic lactone and a boron compound (e.g., U.S. Pat. Nos. 4,963,275 and 4,971,711). The above-mentioned patents are herein incorporated in their entireties.

The TBN of a suitable dispersant may be from about 10 to about 65 mg KOH/g dispersant, on an oil-free basis, which is comparable to about 5 to about 30 TBN if measured on a dispersant sample containing about 50% diluent oil. TBN is measured by the method of ASTM D2896.

In yet other embodiments, the optional dispersant additive may be a hydrocarbyl substituted succinamide or succinimide dispersant. In approaches, the hydrocarbyl substituted succinamide or succinimide dispersant may be derived from a hydrocarbyl substituted acylating agent reacted with a polyalkylene polyamine and wherein the hydrocarbyl substituent of the succinamide or the succinimide dispersant is a linear or branched hydrocarbyl group having a number average molecular weight of about 250 to about 5,000 as measured by GPC using polystyrene as a calibration reference.

In some approaches, the polyalkylene polyamine used to form the dispersant has the Formula

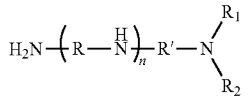

wherein each R and R', independently, is a divalent C1 to C6 alkylene linker, each $R_1$ and $R_2$, independently, is hydrogen, a C1 to C6 alkyl group, or together with the nitrogen atom to which they are attached form a 5- or 6-membered ring optionally fused with one or more aromatic or non-aromatic rings, and n is an integer from 0 to 8. In other approaches, the polyalkylene polyamine is selected from the group consisting of a mixture of polyethylene polyamines having an average of 5 to 7 nitrogen atoms, triethylenetetramine, tetraethylenepentamine, and combinations thereof.

The dispersant, if present, can be used in an amount sufficient to provide up to about 20 wt %, based upon the final weight of the lubricating oil composition. Another amount of the dispersant that can be used may be about 0.1 wt % to about 15 wt %, or about 0.1 wt % to about 10 wt %, about 0.1 to 8 wt %, or about 1 wt % to about 10 wt %, or about 1 wt % to about 8 wt %, or about 1 wt % to about 6 wt %, based upon the final weight of the lubricating oil composition. In some embodiments, the lubricating oil composition utilizes a mixed dispersant system. A single type or a mixture of two or more types of dispersants in any desired ratio may be used.

Antioxidants: The lubricating oil compositions herein also may optionally contain one or more antioxidants. Antioxidant compounds are known and include for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthylamines, alkylated phenyl-alpha-naphthylamines, hindered non-aromatic amines, phenols, hindered phenols, oil-soluble molybdenum compounds, macromolecular antioxidants, or mixtures thereof. Antioxidant compounds may be used alone or in combination.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 available from BASF or an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms. Another commercially available hindered phenol antioxidant may be an ester and may include Ethanox™ 4716 available from Albemarle Corporation.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight, based upon the final weight of the lubricating oil composition. In an embodiment, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In one embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

In another alternative embodiment the antioxidant composition also contains a molybdenum-containing antioxidant in addition to the phenolic and/or aminic antioxidants discussed above. When a combination of these three antioxidants is used, preferably the ratio of phenolic to aminic to molybdenum-containing is (0 to 2):(0 to 2):(0 to 1).

The one or more antioxidant(s) may be present in ranges about 0 wt % to about 20 wt %, or about 0.1 wt % to about 10 wt %, or about 1 wt % to about 5 wt %, of the lubricating oil composition.

Antiwear Agents: The lubricating oil compositions herein also may optionally contain one or more antiwear agents. Examples of suitable antiwear agents include, but are not limited to, a metal thiophosphate; a metal dialkyldithiophosphate; a phosphoric acid ester or salt thereof, a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. A suitable antiwear agent may be a molybdenum dithiocarbamate. The phosphorus containing antiwear agents are more fully described in European Patent 612 839. The metal in the dialkyl dithio phosphate salts may be an alkali metal, alkaline earth metal, aluminum, lead, tin, molybdenum, manganese, nickel, copper, titanium, or zinc. A useful antiwear agent may be zinc dialkyldithiophosphate.

Further examples of suitable antiwear agents include titanium compounds, tartrates, tartrimides, oil soluble amine salts of phosphorus compounds, sulfurized olefins, phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulfides. The tartrate or tartrimide may contain alkyl-ester groups, where the sum of carbon atoms on the alkyl groups may be at least 8. The antiwear agent may in one embodiment include a citrate.

The antiwear agent may be present in ranges including about 0 wt % to about 15 wt %, or about 0.01 wt % to about 10 wt %, or about 0.05 wt % to about 5 wt %, or about 0.1 wt % to about 3 wt % of the lubricating oil composition.

Boron-Containing Compounds: The lubricating oil compositions herein may optionally contain one or more boron-containing compounds. Examples of boron-containing compounds include borate esters, borated fatty amines, borated epoxides, borated detergents, and borated dispersants, such as borated succinimide dispersants, as disclosed in U.S. Pat. No. 5,883,057. The boron-containing compound, if present, can be used in an amount sufficient to provide up to about 8 wt %, about 0.01 wt % to about 7 wt %, about 0.05 wt % to about 5 wt %, or about 0.1 wt % to about 3 wt % of the lubricating oil composition.

Additional Detergents: The lubricating oil composition may optionally further comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds, or methylene bridged phenols. Suitable detergents and their methods of preparation are described in greater detail in numerous patent publications, including U.S. Pat. No. 7,732,390 and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. In some embodiments, a detergent may contain traces of other metals such as magnesium or calcium in amounts such as 50 ppm or less, 40 ppm or less, 30 ppm or less, 20 ppm or less, or 10 ppm or less. A suitable detergent may include alkali or alkaline earth metal salts of petroleum sulfonic acids and long chain mono- or di-alkylarylsulfonic acids with the aryl group being benzyl, tolyl, and xylyl. Examples of suitable detergents include, but are not limited to, calcium phenates, calcium sulfur containing phenates, calcium sulfonates, calcium calixarates, calcium salixarates, calcium salicylates, calcium carboxylic acids, calcium phosphorus acids, calcium mono- and/or di-thiophosphoric acids, calcium alkyl phenols, calcium sulfur coupled alkyl phenol compounds, calcium methylene bridged phenols, magnesium phenates, magnesium sulfur containing phenates, magnesium sulfonates, magnesium calixarates, magnesium salixarates, magnesium salicylates, magnesium carboxylic acids, magnesium phosphorus acids, magnesium mono- and/or di-thiophosphoric acids, magnesium alkyl phenols, magnesium sulfur coupled alkyl phenol compounds, magnesium methylene bridged phenols, sodium phenates, sodium sulfur containing phenates, sodium sulfonates, sodium calixarates, sodium salixarates, sodium salicylates, sodium carboxylic acids, sodium phosphorus acids, sodium mono- and/or di-thiophosphoric acids, sodium alkyl phenols, sodium sulfur coupled alkyl phenol compounds, or sodium methylene bridged phenols.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, or phenols.

An overbased detergent of the lubricating oil composition may have a total base number (TBN) of about 200 mg KOH/gram or greater, or as further examples, about 250 mg KOH/gram or greater, or about 350 mg KOH/gram or greater, or about 375 mg KOH/gram or greater, or about 400 mg KOH/gram or greater. The TBN being measured by the method of ASTM D-2896.

Examples of suitable overbased detergents include, but are not limited to, overbased calcium phenates, overbased calcium sulfur containing phenates, overbased calcium sulfonates, overbased calcium calixarates, overbased calcium salixarates, overbased calcium salicylates, overbased calcium carboxylic acids, overbased calcium phosphorus acids, overbased calcium mono- and/or di-thiophosphoric acids, overbased calcium alkyl phenols, overbased calcium sulfur coupled alkyl phenol compounds, overbased calcium methylene bridged phenols, overbased magnesium phenates, overbased magnesium sulfur containing phenates, overbased magnesium sulfonates, overbased magnesium calixarates, overbased magnesium salixarates, overbased magnesium salicylates, overbased magnesium carboxylic acids, overbased magnesium phosphorus acids, overbased magnesium mono- and/or di-thiophosphoric acids, overbased magnesium alkyl phenols, overbased magnesium sulfur coupled alkyl phenol compounds, or overbased magnesium methylene bridged phenols.

The overbased calcium phenate detergents have a total base number of at least about 150 mg KOH/g, at least about 225 mg KOH/g, at least about 225 mg KOH/g to about 400 mg KOH/g, at least about 225 mg KOH/g to about 350 mg KOH/g or about 230 mg KOH/g to about 350 mg KOH/g, all as measured by the method of ASTM D-2896. When such detergent compositions are formed in an inert diluent, e.g. a process oil, usually a mineral oil, the total base number reflects the basicity of the overall composition including diluent, and any other materials (e.g., promoter, etc.) that may be contained in the detergent composition.

The overbased detergent may have a metal to substrate ratio of from 1.1:1, or from 2:1, or from 4:1, or from 5:1, or from 7:1, or from 10:1. In some embodiments, a detergent is effective at reducing or preventing rust in an engine or other automotive part such as a transmission or gear. The detergent may be present in a lubricating composition at about 0 wt % to about 10 wt %, or about 0.1 wt % to about 8 wt %, or about 1 wt % to about 4 wt %, or greater than about 4 wt % to about 8 wt %.

Extreme Pressure Agents: The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated wax; organic sulfides and polysulfides such as dibenzyldisulfide, bis(chlorobenzyl) disulfide, dibutyl tetrasulfide, sulfurized methyl ester of oleic acid, sulfurized alkyl phenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Friction Modifiers: The lubricating oil compositions herein also may optionally contain one or more friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanadine, alkanolamides, phosphonates, metal-containing compounds, glycerol esters, sulfurized fatty compounds and olefins, sunflower oil other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In some embodiments the friction modifier may be a long chain fatty acid ester. In another embodiment the long chain fatty acid ester may be a mono-ester, or a di-ester, or a (tri)glyceride. The friction modifier may be a long chain fatty amide, a long chain fatty ester, a long chain fatty epoxide derivatives, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g. carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685, herein incorporated by reference in its entirety.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291, herein incorporated by reference in its entirety.

A friction modifier may optionally be present in ranges such as about 0 wt % to about 10 wt %, or about 0.01 wt % to about 8 wt %, or about 0.1 wt % to about 4 wt %.

Molybdenum-containing component: The lubricating oil compositions herein also may optionally contain one or more molybdenum-containing compounds. An oil-soluble molybdenum compound may have the functional performance of an antiwear agent, an antioxidant, a friction modifier, or mixtures thereof. An oil-soluble molybdenum compound may include molybdenum dithiocarbamates, molybdenum dialkyldithiophosphates, molybdenum dithiophosphinates, amine salts of molybdenum compounds, molybdenum xanthates, molybdenum thioxanthates, molybdenum sulfides, molybdenum carboxylates, molybdenum alkoxides, a trinuclear organo-molybdenum compound, and/or mixtures thereof. The molybdenum sulfides include molybdenum disulfide. The molybdenum disulfide may be in the form of a stable dispersion. In one embodiment the oil-soluble molybdenum compound may be selected from the group consisting of molybdenum dithiocarbamates, molybdenum dialkyldithiophosphates, amine salts of molybdenum compounds, and mixtures thereof. In one embodiment the oil-soluble molybdenum compound may be a molybdenum dithiocarbamate.

Suitable examples of molybdenum compounds which may be used include commercial materials sold under the trade names such as Molyvan 822™, Molyvan™ A, Molyvan 2000™ and Molyvan 855™ from R. T. Vanderbilt Co., Ltd., and Sakura-Lube™ S-165, S-200, S-300, S-310G, S-525, S-600, S-700, and S-710 available from Adeka Corporation, and mixtures thereof. Suitable molybdenum components are described in U.S. Pat. No. 5,650,381; US RE 37,363 E1; US RE 38,929 E1; and US RE 40,595 E1, incorporated herein by reference in their entireties.

Additionally, the molybdenum compound may be an acidic molybdenum compound. Included are molybdic acid, ammonium molybdate, sodium molybdate, potassium molybdate, and other alkaline metal molybdates and other molybdenum salts, e.g., hydrogen sodium molybdate, MoOCl4, MoO2Br2, Mo2O3Cl6, molybdenum trioxide or similar acidic molybdenum compounds. Alternatively, the compositions can be provided with molybdenum by molybdenum/sulfur complexes of basic nitrogen compounds as described, for example, in U.S. Pat. Nos. 4,263,152; 4,285,822; 4,283,295; 4,272,387; 4,265,773; 4,261,843; 4,259,195 and 4,259,194; and WO 94/06897, incorporated herein by reference in their entireties.

Another class of suitable organo-molybdenum compounds are trinuclear molybdenum compounds, such as those of the formula Mo3SkLnQz and mixtures thereof, wherein S represents sulfur, L represents independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms may be present among all the ligands' organo groups, such as at least 25, at least 30, or at least 35 carbon atoms. Additional suitable molybdenum compounds are described in U.S. Pat. No. 6,723,685, herein incorporated by reference in its entirety.

The oil-soluble molybdenum compound may be present in an amount sufficient to provide about 0.5 ppm to about 2000 ppm, about 1 ppm to about 700 ppm, about 1 ppm to about 550 ppm, about 5 ppm to about 300 ppm, or about 20 ppm to about 250 ppm of molybdenum.

Transition Metal-containing compounds: In another embodiment, the oil-soluble compound may be a transition metal containing compound or a metalloid. The transition metals may include, but are not limited to, titanium, vanadium, copper, zinc, zirconium, molybdenum, tantalum, tungsten, and the like. Suitable metalloids include, but are not limited to, boron, silicon, antimony, tellurium, and the like.

In an embodiment, an oil-soluble transition metal-containing compound may function as antiwear agents, friction modifiers, antioxidants, deposit control additives, or more than one of these functions. In an embodiment the oil-soluble transition metal-containing compound may be an oil-soluble titanium compound, such as a titanium (IV) alkoxide. Among the titanium containing compounds that may be used in, or which may be used for preparation of the oils-soluble materials of, the disclosed technology are various Ti (IV) compounds such as titanium (IV) oxide; titanium (IV) sulfide; titanium (IV) nitrate; titanium (IV) alkoxides such as titanium methoxide, titanium ethoxide, titanium propoxide, titanium isopropoxide, titanium butoxide, titanium 2-ethylhexoxide; and other titanium compounds or complexes including but not limited to titanium phenates; titanium carboxylates such as titanium (IV) 2-ethyl-1-3-hexanedioate or titanium citrate or titanium oleate; and titanium (IV) (triethanolaminato)isopropoxide. Other forms of titanium encompassed within the disclosed technology include titanium phosphates such as titanium dithiophosphates (e.g., dialkyldithiophosphates) and titanium sulfonates (e.g., alkylbenzenesulfonates), or, generally, the reaction product of titanium compounds with various acid materials to form salts, such as oil-soluble salts. Titanium compounds can thus be derived from, among others, organic acids, alcohols, and glycols. Ti compounds may also exist in dimeric or oligomeric form, containing Ti—O—Ti structures. Such titanium materials are commercially available or can be readily prepared by appropriate synthesis techniques which will be apparent to the person skilled in the art. They may exist at room temperature as a solid or a liquid, depending on the particular compound. They may also be provided in a solution form in an appropriate inert solvent.

In one embodiment, the titanium can be supplied as a Ti-modified dispersant, such as a succinimide dispersant. Such materials may be prepared by forming a titanium mixed anhydride between a titanium alkoxide and a hydrocarbyl-substituted succinic anhydride, such as an alkenyl- (or alkyl) succinic anhydride. The resulting titanate-succinate intermediate may be used directly or it may be reacted with any of a number of materials, such as (a) a polyamine-based succinimide/amide dispersant having free, condensable —NH functionality; (b) the components of a polyamine-based succinimide/amide dispersant, i.e., an alkenyl- (or alkyl-) succinic anhydride and a polyamine, (c) a hydroxy-containing polyester dispersant prepared by the reaction of a substituted succinic anhydride with a polyol, aminoalcohol, polyamine, or mixtures thereof. Alternatively, the titanate-succinate intermediate may be reacted with other agents such as alcohols, aminoalcohols, ether alcohols, polyether alcohols or polyols, or fatty acids, and the product thereof either used directly to impart Ti to a lubricant, or else further reacted with the succinic dispersants as described above. As an example, 1 part (by mole) of tetraisopropyl titanate may be reacted with about 2 parts (by mole) of a polyisobutene-substituted succinic anhydride at 140-150° C. for 5 to 6 hours to provide a titanium modified dispersant or intermediate. The resulting material (30 g) may be further reacted with a succinimide dispersant from polyisobutene-substituted succinic anhydride and a polyethylenepolyamine mixture (127 grams+diluent oil) at 150° C. for 1.5 hours, to produce a titanium-modified succinimide dispersant.

Another titanium containing compound may be a reaction product of titanium alkoxide and $C_6$ to $C_{25}$ carboxylic acid. The reaction product may be represented by the following formula:

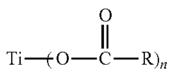

wherein n is an integer selected from 2, 3 and 4, and R is a hydrocarbyl group containing from about 5 to about 24 carbon atoms, or by the formula:

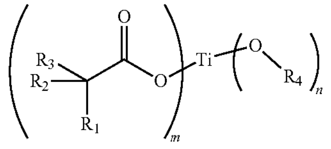

wherein m+n=4 and n ranges from 1 to 3, $R_4$ is an alkyl moiety with carbon atoms ranging from 1-8, $R_1$ is selected from a hydrocarbyl group containing from about 6 to 25 carbon atoms, and $R_2$ and $R_3$ are the same or different and are selected from a hydrocarbyl group containing from about 1 to 6 carbon atoms, or the titanium compound may be represented by the formula:

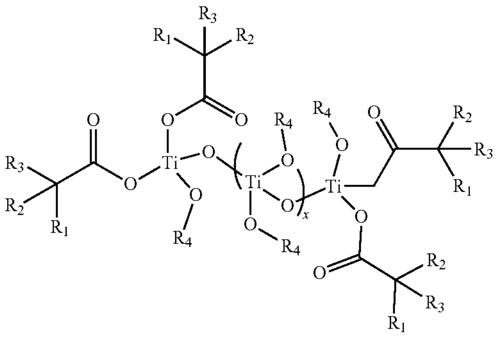

wherein x ranges from 0 to 3, $R_1$ is selected from a hydrocarbyl group containing from about 6 to 25 carbon atoms, $R_2$, and $R_3$ are the same or different and are selected from a hydrocarbyl group containing from about 1 to 6 carbon atoms, and $R_4$ is selected from a group consisting of either H, or $C_6$ to $C_{25}$ carboxylic acid moiety.

Suitable carboxylic acids may include, but are not limited to caproic acid, caprylic acid, lauric acid, myristic acid, palmitic acid, stearic acid, arachidic acid, oleic acid, erucic acid, linoleic acid, linolenic acid, cyclohexanecarboxylic acid, phenylacetic acid, benzoic acid, neodecanoic acid, and the like.

In an embodiment the oil soluble titanium compound may be present in the lubricating oil composition in an amount to provide from 0 to 3000 ppm titanium by weight or 25 to about 1500 ppm titanium by weight or about 35 ppm to 500 ppm titanium by weight or about 50 ppm to about 300 ppm.

Viscosity Index Improvers: The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 20120101017A1.

The lubricating oil compositions herein also may optionally contain one or more dispersant viscosity index improvers in addition to a viscosity index improver or in lieu of a viscosity index improver. Suitable viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt % to about 20 wt %, about 0.1 wt % to about 15 wt %, about 0.1 wt % to about 12 wt %, or about 0.5 wt % to about 10 wt %, of the lubricating oil composition.

Other Optional Additives: Other additives may be selected to perform one or more functions required of a lubricating fluid. Further, one or more of the mentioned additives may be multi-functional and provide functions in addition to or other than the function prescribed herein.

A lubricating oil composition according to the present disclosure may optionally comprise other performance additives. The other performance additives may be in addition to specified additives of the present disclosure and/or may comprise one or more of metal deactivators, viscosity index improvers, detergents, ashless TBN boosters, friction modifiers, antiwear agents, corrosion inhibitors, rust inhibitors, dispersants, dispersant viscosity index improvers, extreme pressure agents, antioxidants, foam inhibitors, demulsifiers, emulsifiers, pour point depressants, seal swelling agents and mixtures thereof. Typically, fully-formulated lubricating oil will contain one or more of these performance additives.

Suitable metal deactivators may include derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles; foam inhibitors including copolymers of ethyl acrylate and 2-ethylhexylacrylate and optionally vinyl acetate; demulsifiers including trialkyl phosphates, polyethylene glycols, polyethylene oxides, polypropylene oxides and (ethylene oxide-propylene oxide) polymers; pour point depressants including esters of maleic anhydride-styrene, polymethacrylates, polyacrylates or polyacrylamides.

Suitable foam inhibitors include silicon-based compounds, such as siloxane.

Suitable pour point depressants may include a polymethylmethacrylates or mixtures thereof. Pour point depressants may be present in an amount sufficient to provide from about 0 wt % to about 1 wt %, about 0.01 wt % to about 0.5 wt %, or about 0.02 wt % to about 0.04 wt % based upon the final weight of the lubricating oil composition.

Suitable rust inhibitors may be a single compound or a mixture of compounds having the property of inhibiting corrosion of ferrous metal surfaces. Non-limiting examples of rust inhibitors useful herein include oil-soluble high molecular weight organic acids, such as 2-ethylhexanoic acid, lauric acid, myristic acid, palmitic acid, oleic acid, linoleic acid, linolenic acid, behenic acid, and cerotic acid, as well as oil-soluble polycarboxylic acids including dimer and trimer acids, such as those produced from tall oil fatty acids, oleic acid, and linoleic acid. Other suitable corrosion inhibitors include long-chain alpha, omega-dicarboxylic acids in the molecular weight range of about 600 to about 3000 and alkenylsuccinic acids in which the alkenyl group contains about 10 or more carbon atoms such as, tetrapropenylsuccinic acid, tetradecenylsuccinic acid, and hexadecenylsuccinic acid. Another useful type of acidic corrosion inhibitors are the half esters of alkenyl succinic acids having about 8 to about 24 carbon atoms in the alkenyl group with alcohols such as the polyglycols. The corresponding half amides of such alkenyl succinic acids are also useful. A useful rust inhibitor is a high molecular weight organic acid.

The rust inhibitor, if present, can be used in an amount sufficient to provide about 0 wt % to about 5 wt %, about 0.01 wt % to about 3 wt %, about 0.1 wt % to about 2 wt %, based upon the final weight of the lubricating oil composition.

In general terms, a suitable lubricant including the neutral to overbased and sulfurized alkyl phenate product herein may include additive components in the ranges listed in the following table.

TABLE 2

Suitable Lubricating Compositions

| Component | Wt. % (Suitable Embodiments) | Wt. % (Suitable Embodiments) |
|---|---|---|
| Improved Overbased Mg sulfonate detergent | 0.02-5.0 | 0.2-2.0 |
| Succinimide Dispersant(s) | 0-8.0 | 1-6.0 |
| Antioxidant(s) | 0.1-5.0 | 0.01-3.0 |
| Other Detergent(s) | 0.0-15.0 | 0.2-8.0 |
| Ashless TBN booster(s) | 0.0-1.0 | 0.01-0.5 |
| Corrosion inhibitor(s) | 0.0-5.0 | 0.0-2.0 |
| Metal dihydrocarbyldithiophosphate(s) | 0.0-6.0 | 0.1-4.0 |
| Ash-free phosphorus compound(s) | 0.0-6.0 | 0.0-4.0 |
| Antifoaming agent(s) | 0.0-5.0 | 0.001-0.15 |
| Antiwear agent(s) | 0.0-1.0 | 0.0-0.8 |
| Pour point depressant(s) | 0.0-5.0 | 0.01-1.5 |
| Viscosity index improver(s) | 0.0-25.0 | 0.1-15.0 |
| Dispersant viscosity index improver(s) | 0.0-10.0 | 0.0-5.0 |
| Friction modifier(s) | 0.00-5.0 | 0.01-2.0 |
| Base oil | Balance | Balance |
| Total | 100 | 100 |

The percentages of each component above represent the weight percent of each component, based upon the weight of the final lubricating oil composition. The remainder of the lubricating oil composition consists of one or more base oils.

Additives used in formulating the compositions described herein may be blended into the base oil individually or in various sub-combinations. However, it may be suitable to blend all of the components concurrently using an additive concentrate (i.e., additives plus a diluent, such as a hydrocarbon solvent). Fully formulated lubricants conventionally contain an additive package, referred to herein as a dispersant/inhibitor package or DI package, that will supply the characteristics that are required in the formulation.

The following definitions of terms are provided in order to clarify the meanings of certain terms as used herein.

The terms “oil composition,” “lubrication composition,” “lubricating oil composition,” “lubricating oil,” “lubricant composition,” “lubricating composition,” “fully formulated lubricant composition,” and “lubricant” are considered synonymous, fully interchangeable terminology referring to the finished lubrication product comprising a major amount of a base oil plus a minor amount of an additive composition.

As used herein, the terms “additive package,” “additive concentrate,” and “additive composition” are considered synonymous, fully interchangeable terminology referring the portion of the lubricating oil composition excluding the major amount of base oil stock mixture.

The term “overbased” relates to metal salts, such as metal salts of sulfonates, carboxylates, salicylates, and/or phenates, wherein the amount of metal present exceeds the stoichiometric amount. Such salts may have a conversion level in excess of 100% (i.e., they may comprise more than 100% of the theoretical amount of metal needed to convert the acid to its “normal,” “neutral” salt). The expression “metal ratio,” often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, salicylates, sulfonates, and/or phenols.

The term “alkaline earth metal” relates to calcium, barium, magnesium, and strontium, and the term “alkali metal” refers to lithium, sodium, potassium, rubidium, and cesium.

As used herein, the term “hydrocarbyl” or “hydrocarbyl substituent” or “hydrocarbyl group” is used in its ordinary sense, which is well-known to those skilled in the art. Specifically, it refers to a group having a carbon atom directly attached to the remainder of the molecule and having a predominantly hydrocarbon character. Each hydrocarbyl group is independently selected from hydrocarbon substituents, and substituted hydrocarbon substituents containing one or more of halo groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents are present for every ten carbon atoms in the hydrocarbyl group.

As used herein, the term “hydrocarbylene substituent” or “hydrocarbylene group” is used in its ordinary sense, which is well-known to those skilled in the art. Specifically, it refers to a group that is directly attached at two locations of the molecule to the remainder of the molecule by a carbon atom and having predominantly hydrocarbon character. Each hydrocarbylene group is independently selected from divalent hydrocarbon substituents, and substituted divalent hydrocarbon substituents containing halo groups, alkyl groups, aryl groups, alkylaryl groups, arylalkyl groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents is present for every ten carbon atoms in the hydrocarbylene group.

As used herein, the term "percent by weight", unless expressly stated otherwise, means the percentage the recited component represents to the weight of the entire composition.

The terms "soluble," "oil-soluble," or "dispersible" used herein may, but does not necessarily, indicate that the compounds or additives are soluble, dissolvable, miscible, or capable of being suspended in the oil in all proportions. The foregoing terms do mean, however, that they are, for instance, soluble, suspendable, dissolvable, or stably dispersible in oil to an extent sufficient to exert their intended effect in the environment in which the oil is employed. Moreover, the additional incorporation of other additives may also permit incorporation of higher levels of a particular additive, if desired.

The term "TBN" as employed herein is used to denote the Total Base Number in mg KOH/g as measured by the method of ASTM D2896.

The term "lime" as employed herein refers to, for example, calcium hydroxide, calcium oxide, and the like compounds, also known as slaked lime or hydrated lime.

The term "alkyl" as employed herein refers to straight, branched, cyclic, and/or substituted saturated chain moieties of from about 1 to about 100 carbon atoms. The term "alkenyl" as employed herein refers to straight, branched, cyclic, and/or substituted unsaturated chain moieties of from about 3 to about 10 carbon atoms. The term "aryl" as employed herein refers to single and multi-ring aromatic compounds that may include alkyl, alkenyl, alkylaryl, amino, hydroxyl, alkoxy, halo substituents, and/or heteroatoms including, but not limited to, nitrogen, oxygen, and sulfur.

The molecular weight for any embodiment herein may be determined with a gel permeation chromatography (GPC) instrument obtained from Waters or the like instrument and the data processed with Waters Empower Software or the like software. The GPC instrument may be equipped with a Waters Separations Module and Waters Refractive Index detector (or the like optional equipment). The GPC operating conditions may include a guard column, 4 Agilent PLgel columns (length of 300×7.5 mm; particle size of 5μ, and pore size ranging from 100-10000 Å) with the column temperature at about 40° C. Un-stabilized HPLC grade tetrahydrofuran (THF) may be used as solvent, at a flow rate of 1.0 mL/min. The GPC instrument may be calibrated with commercially available polystyrene (PS) standards having a narrow molecular weight distribution ranging from 500-380,000 g/mol. The calibration curve can be extrapolated for samples having a mass less than 500 g/mol. Samples and PS standards can be in dissolved in THF and prepared at concentration of 0.1 to 0.5 wt. % and used without filtration. GPC measurements are also described in U.S. Pat. No. 5,266,223, which is incorporated herein by reference. The GPC method additionally provides molecular weight distribution information; see, for example, W. W. Yau, J. J. Kirkland and D. D. Bly, "Modern Size Exclusion Liquid Chromatography", John Wiley and Sons, New York, 1979, also incorporated herein by reference.

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

Example 1

A comparative (e.g., conventional) overbased magnesium sulfonate detergent was prepared by overbasing a C14 to C24 alkyl benzene sulfonic acid using xylene, methanol as a promoter, a molar excess of magnesium oxide, carbon dioxide as the overbasing acid, and with neodecanoic acid at a temperature of about 50 to about 70° C. The mixture was vacuum stripped at about 180° C. to form the comparative overbased magnesium sulfonate detergent having a TBN of about 450 mg KOH/gram, about 9.5 to about 10.5 weight percent magnesium, and a KV100 viscosity of about 9 to about 10 cSt. The unreacted solids were removed by filtration and/or centrifugation. This conventional or comparative detergent was not further post-treated after the vacuum strip.

Example 2

The conventional overbased magnesium sulfonate detergent of Example 1 was then further post-treated at about 180° C. with a polyisobutylene succinic anhydride (PIBSA) where different polyisobutylenes were used that had a number average molecular weight of about 550 g/mol, about 850 g/mol, about 950 g/mol, about 1000 g/mol, or about 2400 g/mol. The polyisobutylene in each instance was considered a HR-PIB having at least about 50 mol % of terminal double bonds. The post-treated overbased magnesium sulfonate detergents were prepared by treating the comparative overbased magnesium sulfonate detergent of Example 1 for about 15 minutes to about 60 minutes at 180° C. with each of the post-treat reactants of Table 2 below.

TABLE 2

| Sample | PIBSA, Mn | Treat Rate of PIBSA during the post-treatment, wt % |
|---|---|---|
| 1 | 2400 | 5% |
| 2 | 2400 | 10% |
| 3 | 950 | 2% |
| 4 | 950 | 8% |
| 5 | 950 | 10% |
| 6 | 1000 | 10% |
| 7 | 850 | 10% |
| 8 | 550 | 10% |

The storage stability of lubricating oil composition including overbased magnesium sulfonate and 0.4 weight percent glycerol monooleate were evaluated at about 55° C. For this study, a control (C) included the comparative or conventional overbased magnesium sulfonate of Example 1 and then the post-treated overbased magnesium sulfonate detergents 1-8 from Example 2 (Table 2) in the same GF-6 lubricant.

To test for storage stability, above 20 to about 25 grams of each lubricant was added to a clear glass vial. Each of the vials was stored at about 55° C. and evaluated for stability once per week (after about 168 hours) for up to 28 weeks. As shown in Table 3 below, a passing stability is designated by a "P" and a failing stability is designated by a "F." Passing means the lubricant was free of sediment, drop-out and film formation. A failing sample means the presence of any sediment (solid particles) or film at the bottom of the vial upon visual examination at the appropriate time (weeks) when using a backlight.

TABLE 3

| Stability Chart | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | Weeks | | | | | | | | | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| C | P | P | P | F | | | | | | | | | | | | | | | | | | | | | | | | |
| 1 | P | P | P | P | P | P | P | P | F | | | | | | | | | | | | | | | | | | | |
| 2 | P | P | P | P | P | P | P | P | P | P | P | P | P | P | P | P | P | F | | | | | | | | | | |
| 3 | P | P | P | P | P | P | P | P | F | | | | | | | | | | | | | | | | | | | |
| 4 | P | P | P | P | P | P | P | P | P | P | P | P | P | P | P | P | P | P | F | | | | | | | | | |
| 5 | P | P | P | P | P | P | P | P | P | P | P | P | P | P | P | P | P | P | P | P | P | P | P | P | P | P | P | F |
| 6 | P | P | P | P | P | P | P | P | P | P | P | P | P | P | P | P | P | P | P | P | P | P | P | P | P | P | F | |
| 7 | P | P | P | P | P | P | P | P | P | P | P | P | P | P | P | F | | | | | | | | | | | | |
| 8 | P | P | P | P | F | | | | | | | | | | | | | | | | | | | | | | | |

As shown by the stability chart of Example 3, the control sample C of conventional overbased magnesium sulfonate and glycerol monooleate (i.e., not post treated) failed stability after only 4 weeks. As shown by Comparative Sample 8, post treatment with a 550 molecular weight PIBSA improved stability, but it only added 1 week. Post treatment with higher molecular weight PIBSA of 850 or even 2400 improved stability, but only up to 17 weeks (i.e., Comparative Samples 1-2 and 7). Inventive Samples 4, 5, and 6 that were post-treated with about 950 to about 1000 g/mol PIBSA at about 8 to about 10 weight percent unexpectedly improved storage stability up to at least 18 weeks (Inventive Sample 4 using about 8 percent of about 950 Mn PIBSA), up to 27 weeks (Inventive Sample 5 using about 10 percent of about 950 Mn PIBSA), and up to 26 weeks (Inventive Sample 6 using about 10 percent of about 1000 Mn PIBSA).

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the end-point values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A method of improving the storage stability of an overbased magnesium sulfonate detergent, the method comprising (a) preparing a mixture of a linear C14 to C24 alkyl benzene sulfonic acid or salt thereof, a molar excess of magnesium oxide or magnesium hydroxide, a C1 to C13 alcohol, and one or more branched C8 to C16 carboxylic acids; carbonating the mixture to form an overbased magnesium sulfonate; vacuum stripping the overbased magnesium sulfonate at about 160° C. to about 200° C.; and treating the vacuum stripped overbased magnesium sulfonate at about 160° C. to about 200° C. with 6 to about 10 weight percent of polyisobutylene succinic anhydride, wherein the polyisobutylene has a number average molecular weight of about 900 to about 1500 and having greater than 50 mol percent of terminal double bonds, to form the overbased magnesium sulfonate detergent; and (b) combining about 0.02 to about 5 weight percent of the overbased magnesium sulfonate detergent with up to about 0.4 of glycerol monooleate friction modifier; and wherein the combination of the overbased magnesium sulfonate detergent and the glycerol monooleate friction modifier is storage stable at about 55° C. for at least about 18 weeks.

2. The method of claim 1, wherein the overbased magnesium sulfonate prior to the treating has a total base number (TBN) of at least about 450 mg KOH/g and the overbased magnesium sulfonate detergent after the treating has a total base number (TBN) of less than about 410 mg KOH/g.

3. The method of claim 2, wherein the overbased magnesium sulfonate detergent includes at least about 60 weight percent of magnesium sulfonate as an active ingredient.

4. The method of claim 3, wherein the overbased magnesium sulfonate detergent has about 35 weight percent or less of process oil.

5. The method of claim 1, wherein the treating step (c) is substantially free of dicarboxylic acids.

6. The method of claim 5, wherein the dicarbocylic acids are one or more of phthalic acid, succinic acid, maleic acid, azelaic acid, suberic acid, sebasic acid, fumaric acid, adipic acid, malonic acid, or combinations thereof.

7. The method of claim 1, wherein the overbased magnesium sulfonate detergent has a total base number (TBN) of about 350 to about 410 mg KOH/g and is storage stable at about 55° C. when combined with up to about 0.4 weight percent of glycerol monooleate friction modifier for at least about 18 weeks.

* * * * *